United States Patent
Fonte et al.

(10) Patent No.: US 9,907,657 B2
(45) Date of Patent: *Mar. 6, 2018

(54) POROUS COATING FOR ORTHOPEDIC IMPLANT UTILIZING POROUS, SHAPE MEMORY MATERIALS

(71) Applicant: Arthrex, Inc., Naples, FL (US)

(72) Inventors: Matthew Fonte, Concord, MA (US); Matthew Palmer, Cambridge, MA (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/063,885

(22) Filed: Mar. 8, 2016

(65) Prior Publication Data

US 2016/0184103 A1 Jun. 30, 2016

Related U.S. Application Data

(63) Continuation-in-part of application No. 13/764,188, filed on Feb. 11, 2013, now Pat. No. 9,278,000.

(60) Provisional application No. 61/596,900, filed on Feb. 9, 2012.

(51) Int. Cl.
| | | |
|---|---|---|
| A61F 2/28 | (2006.01) |
| A61F 2/30 | (2006.01) |
| A61F 2/36 | (2006.01) |
| A61F 2/44 | (2006.01) |
| A61L 27/30 | (2006.01) |
| A61L 27/56 | (2006.01) |

(52) U.S. Cl.
CPC ...... *A61F 2/30767* (2013.01); *A61F 2/30734* (2013.01); *A61F 2/36* (2013.01); *A61F 2/4455* (2013.01); *A61L 27/306* (2013.01); *A61L 27/56* (2013.01); *A61F 2002/30011* (2013.01); *A61F 2002/30092* (2013.01); *A61F 2002/30738* (2013.01); *A61F 2002/30769* (2013.01); *A61F 2002/30909* (2013.01); *A61F 2002/30911* (2013.01); *A61F 2002/30929* (2013.01); *A61F 2210/0014* (2013.01); *A61L 2400/16* (2013.01); *A61L 2430/02* (2013.01); *A61L 2430/24* (2013.01)

(58) Field of Classification Search
CPC ...... A61F 2/32; A61F 2/36; A61F 2/38; A61F 2/389; A61F 2/44; A61F 2/4455; A61F 2/30767; A61F 2/3859

See application file for complete search history.

(56) References Cited

U.S. PATENT DOCUMENTS

| | | | | |
|---|---|---|---|---|
| 5,986,169 A * | 11/1999 | Gjunter | ............... | A61L 27/06 424/422 |
| 6,619,877 B1 * | 9/2003 | Huang | ............... | B25G 1/04 16/429 |
| 6,913,622 B2 * | 7/2005 | Gjunter | ............... | A61F 2/442 623/17.16 |
| 6,929,866 B1 * | 8/2005 | Williams | ............ | C04B 41/5071 428/307.7 |
| 7,875,070 B2 | 1/2011 | Molaei | | |
| 7,947,135 B2 * | 5/2011 | Fonte | ............... | A61F 2/30942 148/563 |

(Continued)

Primary Examiner — Alvin Stewart
(74) Attorney, Agent, or Firm — Carlson, Gaskey & Olds, P.C.

(57) ABSTRACT

A porous coating for a medical implant, wherein the porous coating comprises a porous, shape memory material.

26 Claims, 21 Drawing Sheets

Hip Implant in the Femoral Canal with a Porous Coating bonding/interfacing to the Implant and Bone Tissue Nitinol (shape memory alloy), superelastic honeycomb structure

(56) References Cited

U.S. PATENT DOCUMENTS

| | | | |
|---|---|---|---|
| 7,976,648 B1 | 7/2011 | Boylan et al. | |
| 8,062,378 B2* | 11/2011 | Fonte | A61F 2/30942 |
| | | | 623/23.11 |
| 8,137,486 B2* | 3/2012 | Fonte | A61F 2/30942 |
| | | | 148/563 |
| 8,216,398 B2 | 7/2012 | Bledsoe et al. | |
| 8,398,790 B2* | 3/2013 | Fonte | A61F 2/30942 |
| | | | 148/402 |
| 8,425,588 B2 | 4/2013 | Molaei | |
| 8,585,770 B2* | 11/2013 | Meridew | A61F 2/30724 |
| | | | 623/22.11 |
| 8,721,646 B2 | 5/2014 | Fox | |
| 9,017,331 B2 | 4/2015 | Fox | |
| 9,155,819 B2* | 10/2015 | Fonte | A61L 27/56 |
| 9,278,000 B2* | 3/2016 | Fonte | A61L 27/00 |
| 9,339,268 B2 | 5/2016 | Fox | |
| 2002/0077701 A1* | 6/2002 | Kuslich | A61F 2/441 |
| | | | 623/17.12 |
| 2005/0031704 A1* | 2/2005 | Ahn | A61K 33/42 |
| | | | 424/602 |
| 2007/0123976 A1* | 5/2007 | Yuan | A61L 27/06 |
| | | | 623/1.39 |
| 2008/0243264 A1* | 10/2008 | Fonte | A61F 2/30942 |
| | | | 623/22.43 |
| 2008/0290141 A1* | 11/2008 | Shaw | B23K 1/0008 |
| | | | 228/155 |
| 2009/0182336 A1* | 7/2009 | Brenzel | A61B 17/7225 |
| | | | 606/62 |
| 2010/0057197 A1* | 3/2010 | Weber | A61L 27/30 |
| | | | 623/1.42 |
| 2010/0203155 A1* | 8/2010 | Wei | A61F 2/4603 |
| | | | 424/549 |
| 2010/0255053 A1* | 10/2010 | Savage-Erickson | A61L 27/12 |
| | | | 424/423 |
| 2011/0071633 A1* | 3/2011 | Fonte | A61F 2/30767 |
| | | | 623/16.11 |
| 2011/0118850 A1* | 5/2011 | Govil | A61F 2/4644 |
| | | | 623/23.61 |
| 2012/0029102 A1* | 2/2012 | Rose | A61B 17/72 |
| | | | 521/88 |
| 2013/0035761 A1* | 2/2013 | Sharkey | A61B 17/56 |
| | | | 623/17.11 |
| 2013/0211533 A1* | 8/2013 | Fonte | A61L 27/00 |
| | | | 623/22.4 |
| 2013/0218288 A1* | 8/2013 | Fonte | A61L 27/56 |
| | | | 623/23.5 |
| 2014/0257420 A1 | 9/2014 | Fox | |
| 2014/0324048 A1 | 10/2014 | Fox | |
| 2014/0358244 A1* | 12/2014 | Hakansson | A61F 2/4261 |
| | | | 623/21.12 |
| 2016/0081803 A1* | 3/2016 | McKay | A61L 27/46 |
| | | | 623/23.61 |
| 2016/0135955 A1* | 5/2016 | Henderson | A61L 27/16 |
| | | | 623/23.61 |
| 2016/0158417 A1* | 6/2016 | Fonte | A61L 27/56 |
| | | | 623/23.57 |
| 2016/0184103 A1* | 6/2016 | Fonte | A61L 27/306 |
| | | | 623/23.5 |
| 2017/0014169 A1* | 1/2017 | Dean | A61B 34/10 |
| 2017/0021060 A1* | 1/2017 | Grunlan | A61L 27/50 |
| 2017/0071742 A1* | 3/2017 | Palmer | A61F 2/2846 |

\* cited by examiner

Hip Implant in the Femoral Canal with a Porous Coating bonding/interfacing to the Implant and Bone Tissue Trabecular bone with interconnecting pores Cell Structure Similar to Trabecular Bone Open Cell Carbon Foam Materials

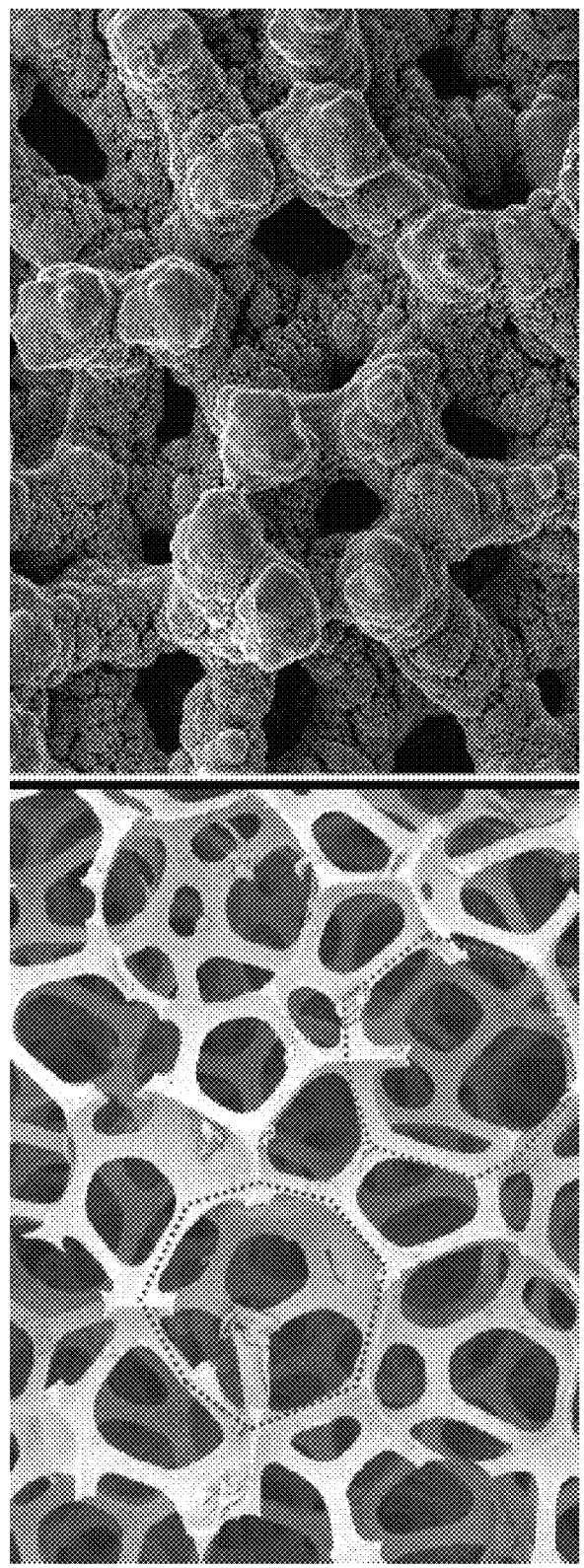
FIG. 9 Shape Memory Material Coated Foam
FIG. 8 Polyurethane Foam with Dodecahedron Structure Nitinol (shape memory alloy), superelastic honeycomb structure 3D dodecahedron honeycomb coating made of SMM 3D dodecahedron structure

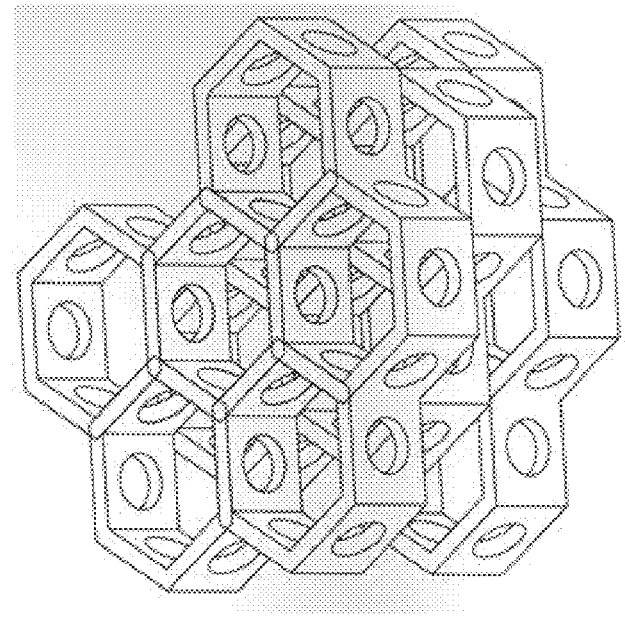
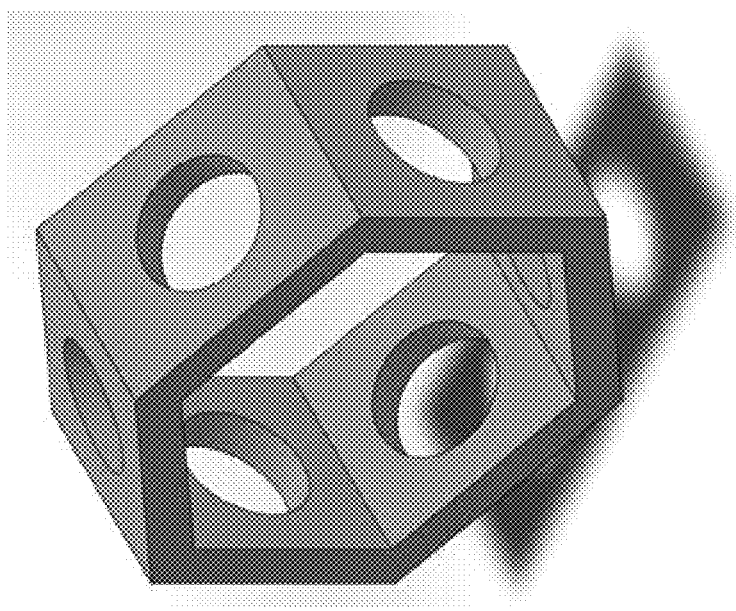
Many Elements Stacked Together
Hexagonal Functional Unit
FIG. 13

Many Elements Stacked Together

Diamond Shaped Functional Unit

Austenite phase, martensite phase and deformed martensite phase

POROUS COATING FOR ORTHOPEDIC IMPLANT UTILIZING POROUS, SHAPE MEMORY MATERIALS

REFERENCE TO PENDING PRIOR PATENT APPLICATION

This patent application is a continuation-in-part of pending prior U.S. patent application Ser. No. 13/764,188, filed Feb. 11, 2013 by MX Orthopedics, Corp. and Matthew Fonte et al. for POROUS COATING FOR ORTHOPEDIC IMPLANT UTILIZING POROUS, SHAPE MEMORY MATERIALS, which patent application claims benefit of prior U.S. Provisional Patent Application Ser. No. 61/596,900, filed Feb. 9, 2012 by Matthew Fonte et al. for POROUS, SHAPE MEMORY MATERIAL, ORTHOPEDIC IMPLANT COATING.

The two (2) above-identified patent applications are hereby incorporated herein by reference.

BACKGROUND OF THE INVENTION

Many orthopedic implants have a coating on their surface to enhance osseointegration. These include, but are not limited to, hip, knee, shoulder, spine, extremities, and dental implants. These implants are typically made from stainless steel alloys, cobalt-chrome alloys, titanium alloys, or polymers such as polymers in the polyaryletherketone family (e.g, polyether ether ketone (PEEK), polyetherketone (PEK), polyetherketoneketone (PEKK), polyetheretherketomeketone (PEEKK) and polyetherketoneetherketoneketone (PEKEKK)), and polyethylenes. Historically, many implants were cemented in place using Polymethyl methacrylate. Today, surgeons generally prefer to rely on osseointegration to hold implants in place.

As an example, today hip implant stems are typically a composite structure consisting of either a cobalt-chrome alloy or titanium alloy substrate that carries the patient's weight, with a textured surface coating composed largely of peaks and valleys to aid in immediate fixation and ultimately promote and facilitate long term osseointegration. See FIG. 1.

Furthermore, there are many PEEK implants which are used for spinal procedures. To enhance the osseointegration of the PEEK, companies have introduced titanium plasma spray coatings to the PEEK implants.

Today, the majority of implant coatings are textured coatings, which are applied by hot plasma spray, vapor deposition (chemical and/or physical), or by sintering fiber mesh or beads. See FIG. 2.

These coatings processes leave a largely two-dimensional structure for the bone to grow around. There is no means for the bone to tunnel further into the coating so as to establish significant three-dimensional osseointegration. This may stifle or compromise long-term osseointegration. Additionally, the largely two-dimensional structures created using these technologies do not closely mimic the structure of trabecular bone, which is a three-dimensional structure with interconnecting networks of pores having capillarity properties. See FIG. 3.

Recently, there have been advances in the creation of porous coatings that more accurately resemble trabecular bone. These porous surface coatings have interconnecting networks of pores which are similar to those of trabecular bone, and may serve to promote bone ingrowth deeper into the porous coating and provide better long-term implant fixation. There are several techniques known in the art for creating these porous coatings. One method is to coat a structure similar to trabecular bone, e.g., a polyurethane foam, with powdered titanium through low temperature arc vapor deposition (LTAVD) or chemical vapor deposition or sputtering, and then to sinter the resulting structure onto the substrate (e.g., the hip implant). See FIG. 4.

Other methods include chemical vapor deposition of commercially pure tantalum onto a porous carbon scaffold and then sintering the resulting structure onto the substrate (e.g., the hip implant). See FIGS. 5 and 6.

In addition to these porous metal constructs being used as coatings, they can also be used as standalone implants. By way of example but not limitation, these porous metal constructs can serve as bone void fillers, cement spacers, femoral and tibial cone augments, buttresses, cages, spine interbody fusion devices and other bone augmentation devices including bone wedges such as Cotton and Evans wedges.

Often these standalone implants find utility in revision procedures following a primary implant failure. Removal of the primary implant leaves a large void that needs to be filled. These porous metal implants can be used to fill these voids and provide a support structure for the new implant.

SUMMARY OF THE INVENTION

Femoral stems with reduced stiffness have been introduced in total hip arthroplasty to facilitate proximal load transfer and thereby reduce stress shielding and periprosthetic bone loss. Poor fixation and unacceptably high revision rates are a major problem with these reduced stiffness femoral stem prostheses. A purpose of the present invention is to improve early performance of femoral implants by creating an implant with a dynamic surface coating that is both less stiff to address stress shielding and expands after implantation to improve fixation (for the purposes of the present invention, the term "dynamic" may be considered to mean capable of changing shape, e.g., due to structural resilience, including superelasticity, thermal shape recovery, etc.). The dynamic surface coating consists of a shape memory material, e.g., Nitinol, near beta or fully beta titanium alloys, shape memory polymers (thermoplastic block copolymers) and biodegradable shape memory polymer systems, all of which can be processed to have superelasticity and/or shape recovery. These dynamic surface coatings have a 2D or 3D porous structure which proximally cover the femoral stem. The pores of the dynamic surface coatings can be infiltrated with a mixture of hydroxyapatite, tricalcium phosphate and other bone-promoting agents known in the art. This invention also finds utility as a dynamic surface coating in other orthopedic implants where fixation and osseointegration are essential, e.g., knee implants, shoulder implants, elbow implants, spinal implants, maxillofacial implants, cranial implants, extremity (e.g., fingers and toes) implants, etc.

In addition to the foregoing, and as noted above, porous metals have not only been used as coatings on implants but have also been used as the implant itself. Porous metal implants have been introduced into a void in bone to act as bone void fillers and bone augmentation devices. These porous metal implants are often used as part of a revision procedure after the primary implant has failed and has been removed. Removal of the implant leaves behind a void in the bone. Instead of filling this void with bone cements, it has become popular to implant a porous metal implant to fill some of the space in the bone and to provide support for the revision implant. Bone thereafter grows into the porous metal implant, securely holding the porous metal implant in place, typically adjacent to the revision implant.

Porous metal implants have also been used as wedges for osteotomies. In these procedures an opening wedge osteotomy is performed and the porous metal implant is used to keep the osteotomy open. The porous metal composition of the wedge allows for bone ingrowth and eventual fusion of the osteotomy site.

Current porous metal implants are static and are unable to conform to the geometry of the anatomy. Thus it has been observed that gaps exist between the implants and the bone. This greatly impairs the bone's ability to grow into the porous metal scaffold. This is especially true for porous metal implants used as part of a revision procedure. Removal of a primary implant often creates an irregularly-shaped bone void which is difficult to completely fill using a conventional porous metal implant.

Thus there exists a clinical need for dynamic porous metal implants that are able to conform to implantation sites so as to maximize the surface area of implant-bone contact. These dynamic porous metal implants may also be less stiff to address stress shielding. Also, they may be elastic and attempt to expand after implantation so as to improve implant fixation and to apply stress to the adjacent bone so as to enhance bone remodeling and ingrowth.

The present invention provides a novel dynamic porous implant that consists of a shape memory material, e.g., Nitinol, near beta or fully beta titanium alloys, shape memory polymers (thermoplastic block copolymers) and biodegradable shape memory polymer systems, all of which can be processed to have superelasticity and/or shape recovery. These dynamic porous implants comprise a 3D porous structure. The pores can be infiltrated with a mixture of hydroxyapatite, tricalcium phosphate and other bone-promoting agents known in the art. This invention finds utility as a dynamic porous implant where fixation and osseointegration are essential, e.g., bone void fillers, cement spacers, femoral and tibial cone augments, buttresses, cages and other bone augmentation devices including bone wedges such as Cotton and Evans wedges.

In one preferred form of the invention, there is provided a porous coating for a medical implant, wherein the porous coating comprises a porous, shape memory material.

In another preferred form of the invention, there is provided a medical implant comprising a body and a porous coating secured to a surface of the body, wherein the porous coating comprises a porous, shape memory material.

In another preferred form of the invention, there is provided a method for providing therapy to a patient, the method comprising:

providing a medical implant comprising a body and a porous coating secured to a surface of the body, wherein the porous coating comprises a porous, shape memory material; and inserting the medical implant into the patient so that the porous coating applies an outward force against adjacent bone so as to fill gaps between the porous coating and adjacent bone and to create an interference fit between the medical implant and the adjacent bone.

In another preferred form of the invention, there is provided a method for providing therapy to a patient, the method comprising:

providing a medical implant comprising a dynamic porous material, wherein the dynamic porous material comprises a porous structure formed of a shape memory material; and inserting the medical implant into the patient so that the dynamic porous implant applies an outward force against adjacent bone so as to create an interference fit between the medical implant and the adjacent bone.

In another preferred form of the invention, there is provided a medical implant comprising a dynamic porous material, wherein the dynamic porous material comprises a porous structure formed of a shape memory material, the medical implant being configured for insertion into a patient so that the dynamic porous implant applies an outward force against adjacent bone so as to create an interference fit between the medical implant and the adjacent bone.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings, wherein like numbers refer to like parts and further wherein:

FIG. 8 is a schematic view showing a polyurethane foam with a dodecahedron structure;

FIG. 9 is a schematic view showing porous foam coated with a shape memory material;

FIG. 13 is a schematic view showing a hexagonal functional unit, and a structure formed out of a plurality of hexagonal functional units assembled together;

DETAILED DESCRIPTION OF THE PREFERRED EMBODIMENTS

Novel Shape Memory Material Coating

Today surface coatings are static which limits their ability to infiltrate the bone tissue. As such, bone tissue must infiltrate the coating in order to achieve some level of osseointegration. In contrast, the present invention is a porous coating that is dynamic, made of shape memory materials (SMM), e.g., Nitinol (NiTi) per ASTM F2063, Ti-13Nb-13Zr per ASTM F1713, Ti-12Mo-6Zr-2Fe (TMZF) per ASTM F1813, etc., that expands and applies strain against the bone tissue so as to facilitate bone remodeling and expedite/enhance osseointegration. Thus, the dynamic porous coating of the present invention applies bone-building strain against the bone tissue and, in the process, stimulates bone remodeling and osseointegration into the porous coating. SMM coatings with open porosity offer the following advantageous properties: (i) good biocompatibility, (ii) a combination of high strength which is important to prevent deformation or fracture, relatively low stiffness which is useful to minimize stress shielding effects, and high toughness which is essential to avoid brittle failure, (iii) a porous scaffold for bony ingrowth; and (iv) shape-recovery behavior facilitating implant insertion and ensuring good mechanical stability within the host tissue. The shape memory material surface coating can be produced by any method known in the art, and may include the coating of an analog trabecular structure, e.g., a polyurethane foam, with a deposited powder Nitinol (NiTi) coating accomplished through low temperature arc vapor deposition (LTAVD) and sintering the resulting porous structure onto the substrate (hip implant).

Figure 1:
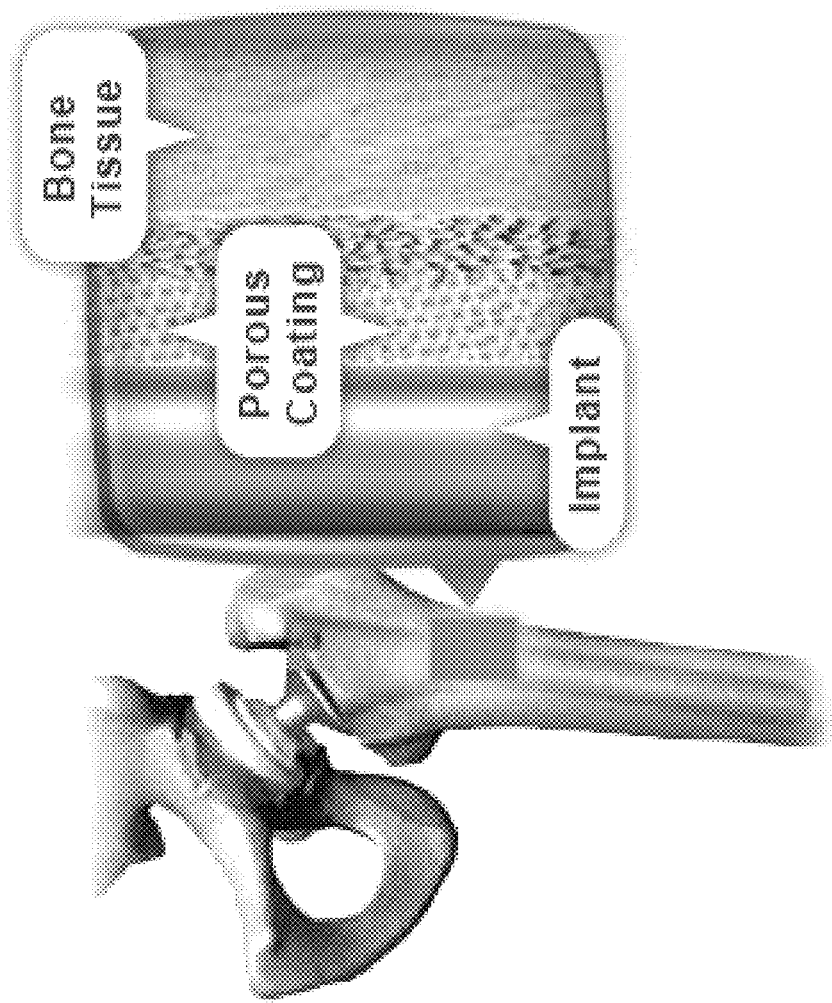
FIG. 1 is a schematic view showing a typical orthopedic implant having a porous coating.
Figure 2:
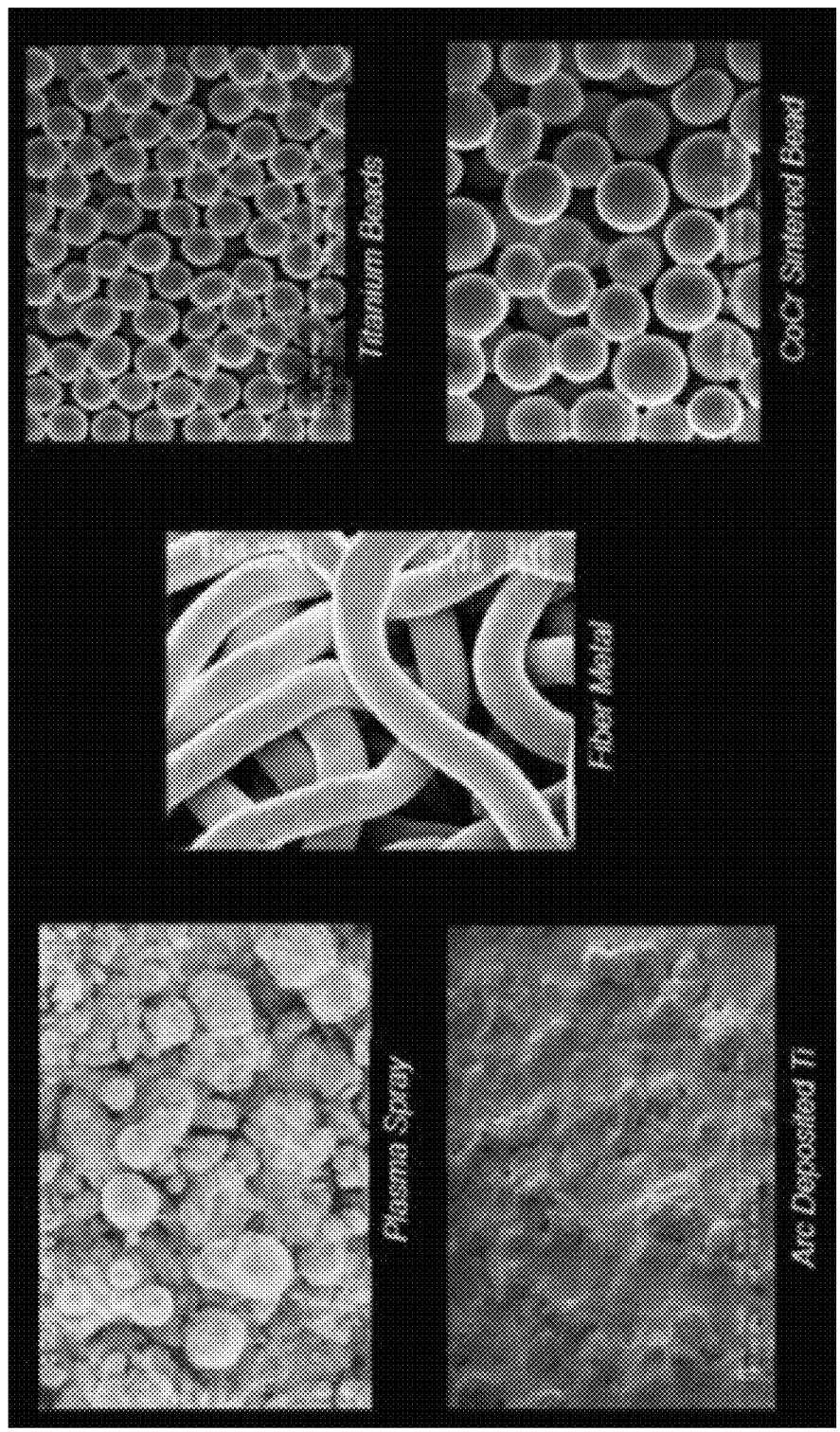
FIG. 2 is a schematic view showing various approaches for forming a porous coating for an orthopedic implant.
Figure 3:
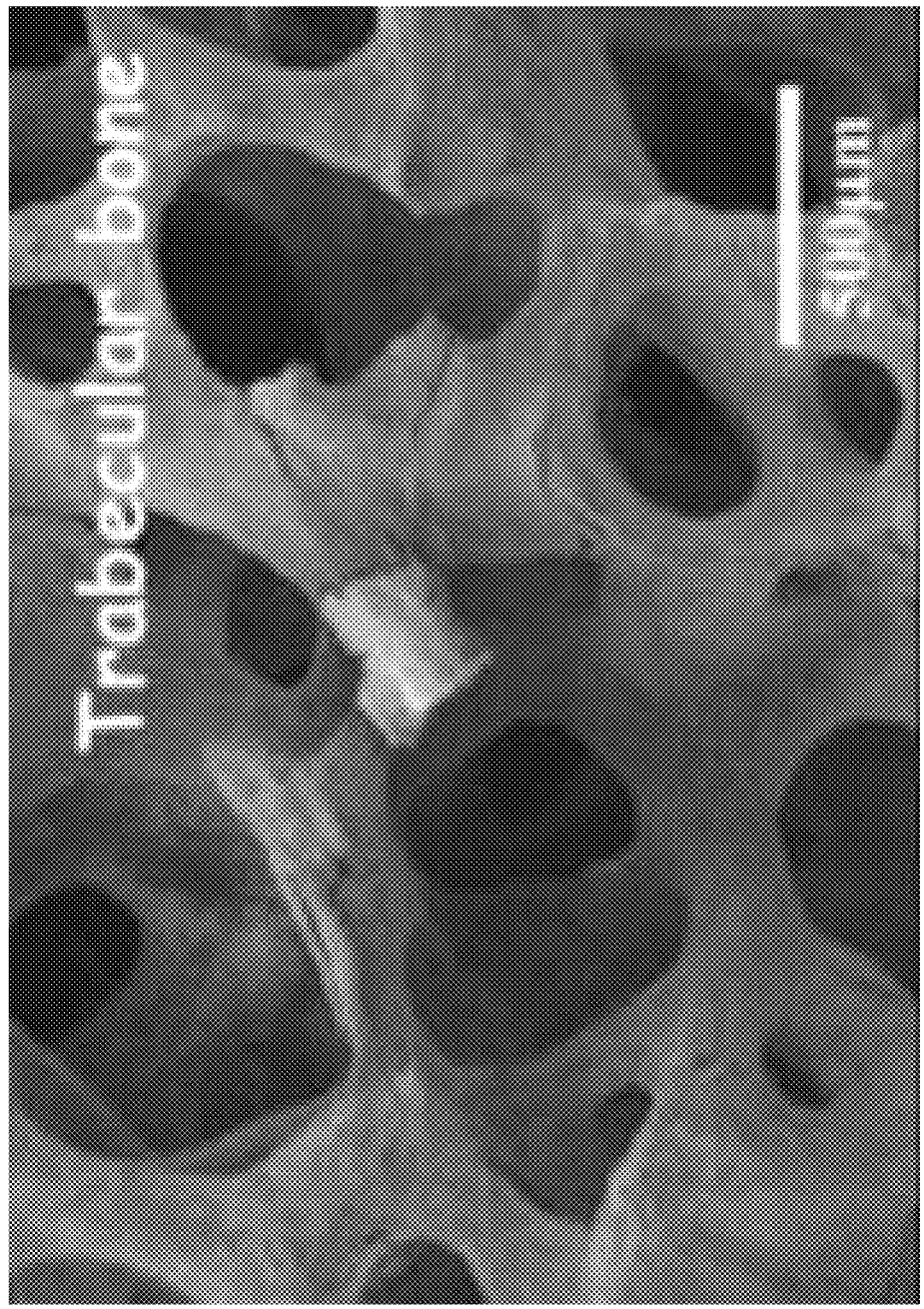
FIG. 3 is a schematic view showing trabecular bone with interconnecting pores.
Figure 4:
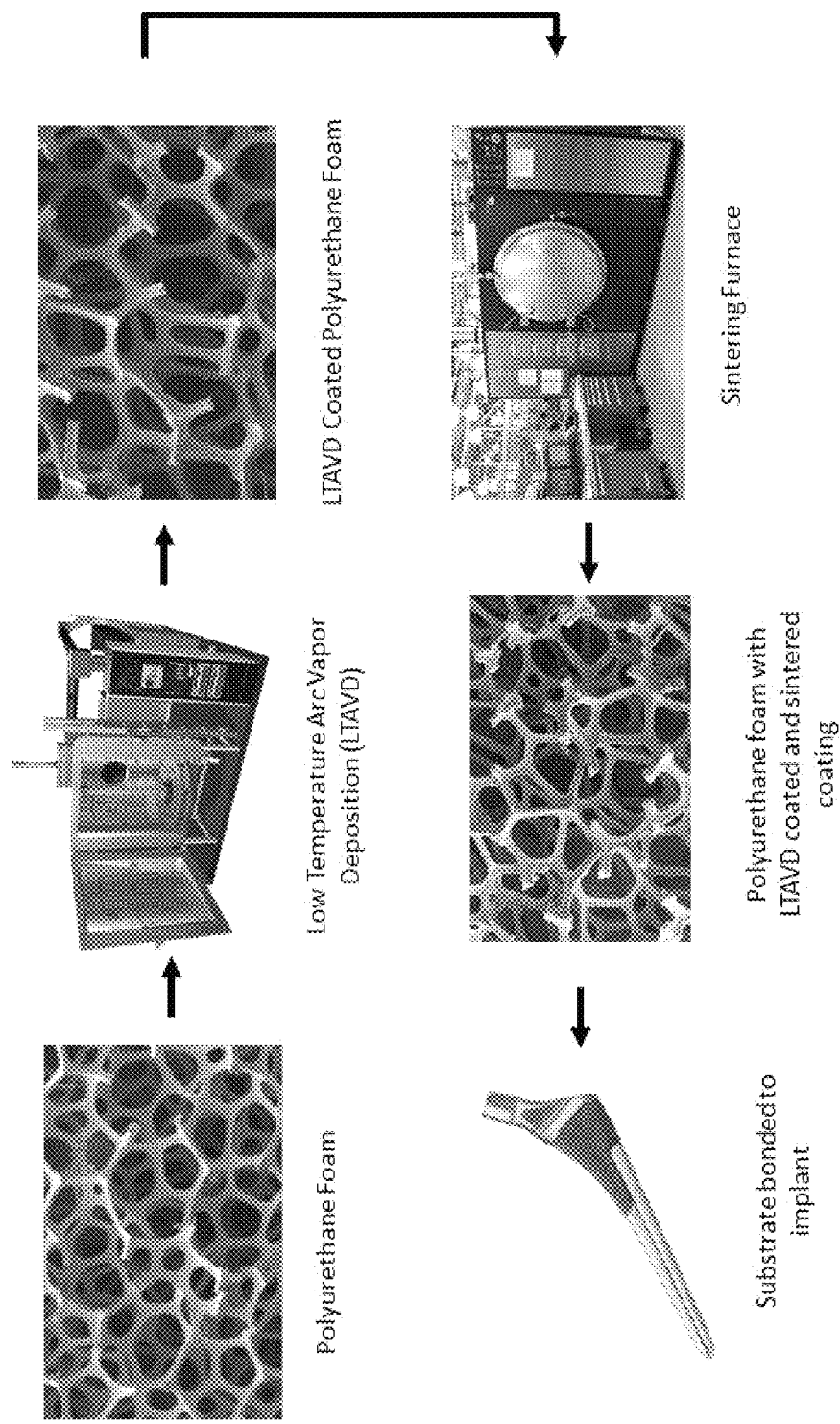
FIG. 4 is a schematic view showing how a porous coating may be formed by depositing powdered titanium on a polyurethane foam, and then sintering the resulting structure onto an orthopedic implant.
Figure 6:
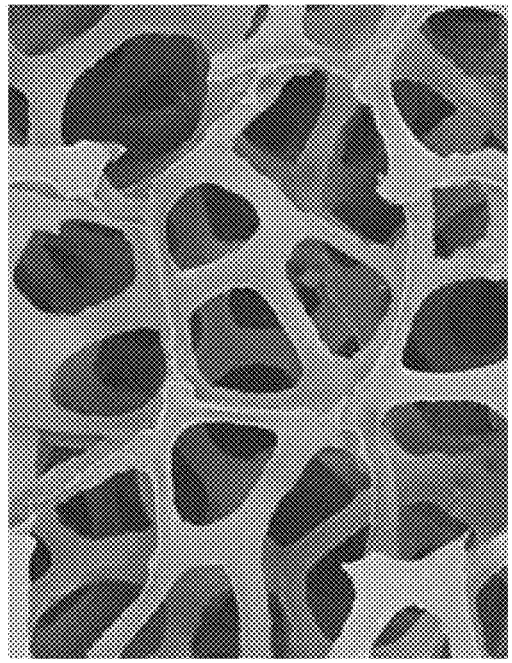
FIGS. 5 and 6 are schematic views showing how tantalum may be chemically vapor deposited onto an open cell carbon foam so as to form a structure analogous to trabecular bone.
Figure 5:
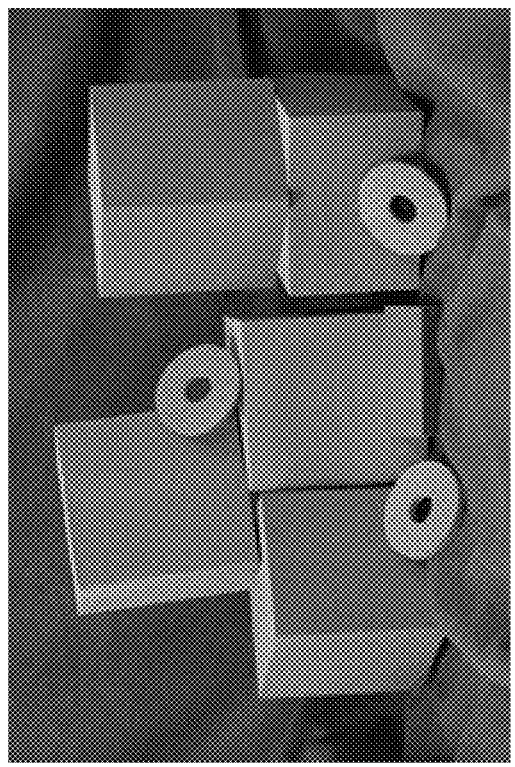
Figure 7:
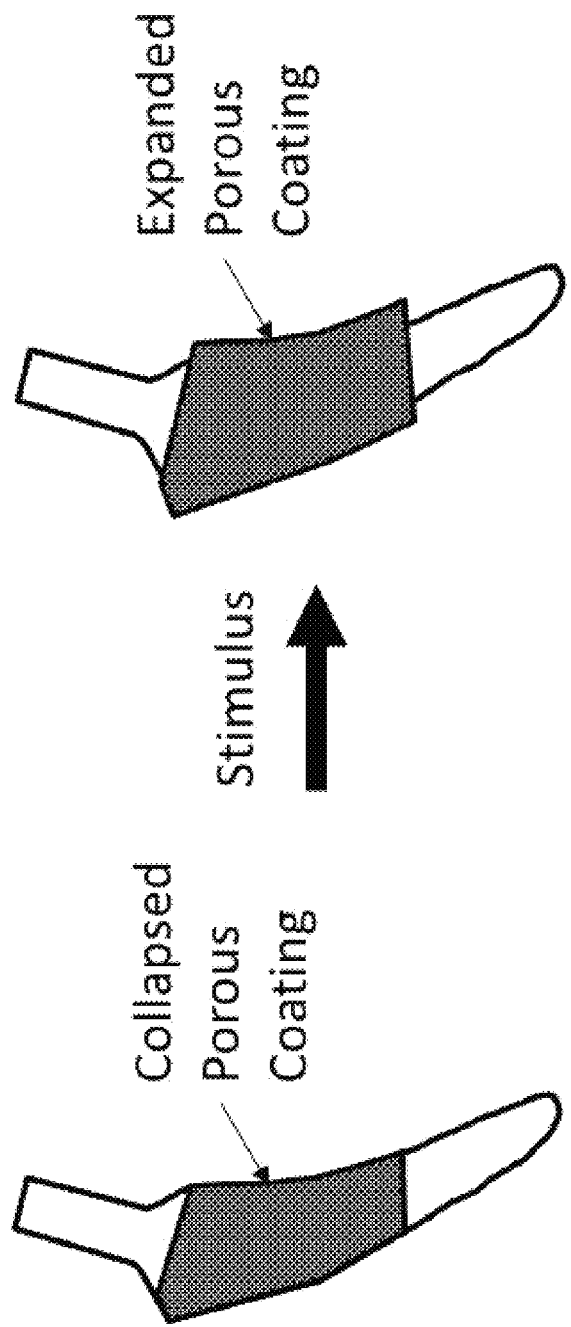
FIG. 7 is a schematic view showing an orthopedic implant having a porous coating formed out of shape memory material, with the porous coating capable of assuming a collapsed state and an expanded state.

The NiTi-coated exoskeleton structure can be superelastic (SE) which is capable of restoring its shape once it is unconstrained and made to spring back, and/or it can have shape memory effect (SME) which allows it to be dynamic under the influence of temperature change. The trabecular coated surface of the implant can be "squished" flat and either superelastically, or through SME (temperature change), spring outward once inserted into the femoral canal so as to put pressure on the bone tissue and lock the implant in place. The SMM coating can be applied to static implants made of cobalt-chrome alloys and titanium alloys; or the SMM coating can be applied to dynamic implants made of shape memory material like Nitinol. See FIG. 7.

The polyurethane foam that has been coated with the shape memory material has a basic dodecahedron structure. See FIGS. 8 and 9.

The yield strength and elastic modulus of the dodecahedron coating made of SMM can be engineered to desirably match the stiffness of bone by modifying the cell size, struts' thickness, width and length; and by modifying the amount and position of the packed "buckyball" structure in relation to one another. The SMM coating can have an elastic modulus at approximately 1-20 GPa.

| Paired measurements of elastic modulus and tensile yield strain of trabecular tissue and cortical bone | | | | | |
|---|---|---|---|---|---|
| Elastic modulus (GPa) | | Tensile yield strain$^a$ (%) | | Tensile yield stress$^a$ (MPa) | |
| Trabecular | Cortical | Trabecular | Cortical | Trabecular | Cortical |
| 21.1 | 20.3 | 0.65 | 0.74 | 95.6 | 111.4 |
| 22.2 | 18.9 | 0.62 | 0.76 | 93.6 | 106.8 |
| 19.3 | 20.9 | 0.60 | 0.75 | 77.4 | 114.3 |
| 17.8 | 19.8 | N/A$^c$ | 0.71 | N/A$^c$ | 104.9 |

Figure 10:
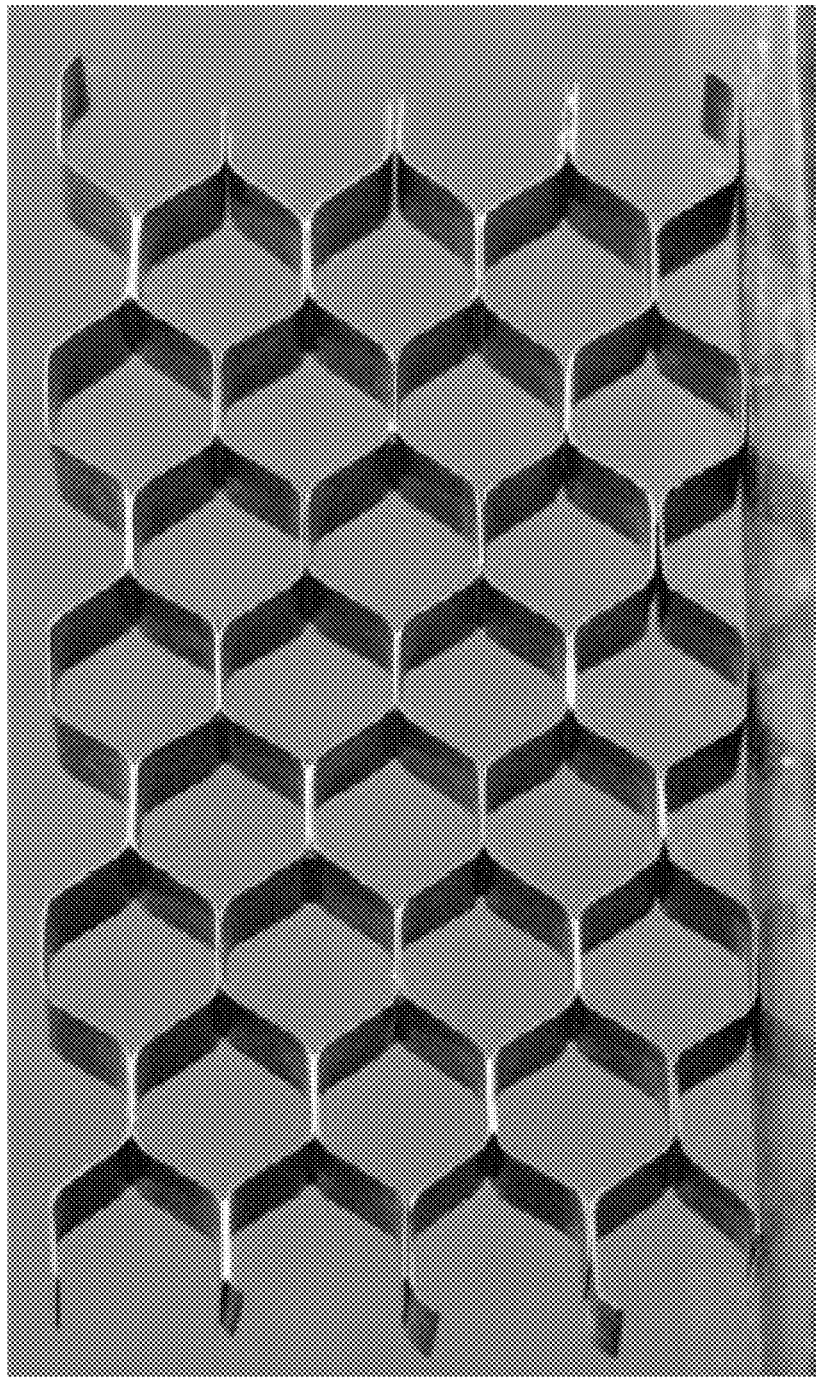
FIG. 10 is a schematic view showing a honeycomb structure formed out of a shape memory material.

Another method of producing the dynamic, expanding porous coating is to use a honeycomb, cellular structure made from SMMs for their SE and SME properties. Like the "buckyball" coated structure, the yield strength and Elastic Modulus of the honeycomb structure made of SMM can be engineered to also match the stiffness of bone by modifying the cell size and strut thickness, width, and length. See FIG. 10.

Figure 12:
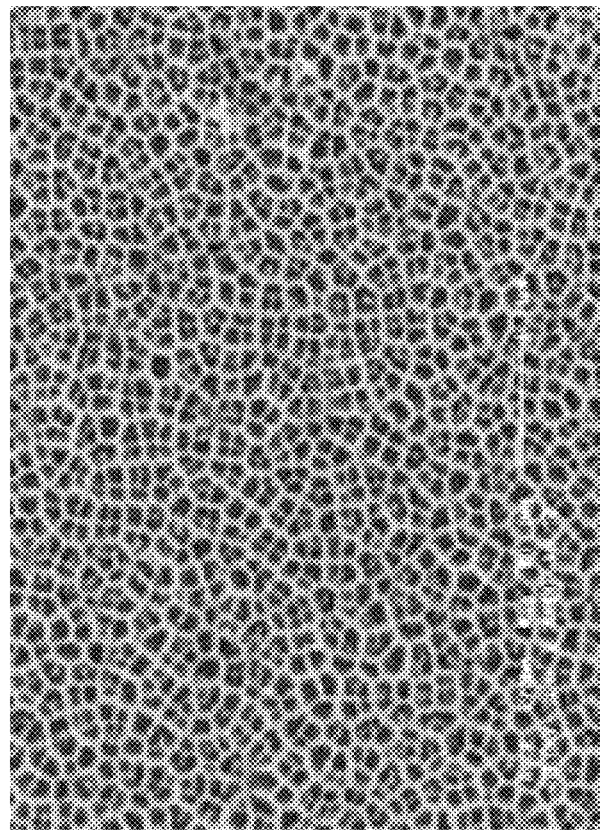
FIG. 12 is a schematic view showing a 3D dodecahedron structure formed out of a shape memory material.
Figure 11:
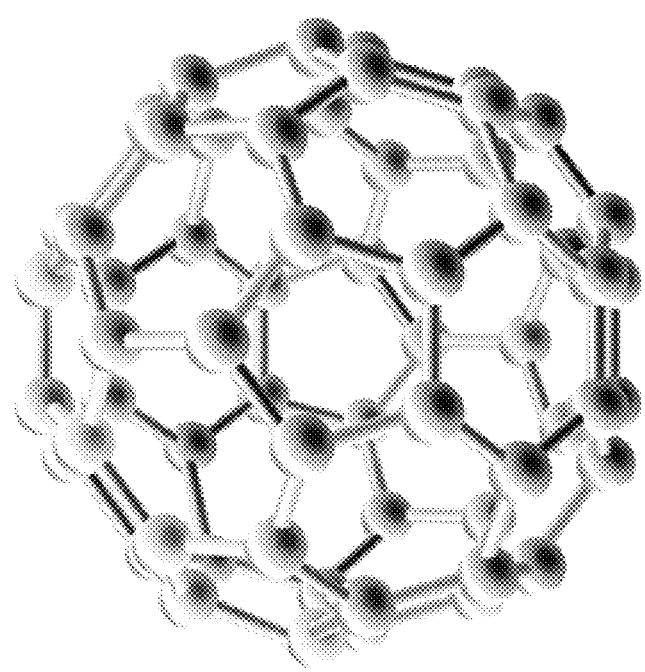
FIG. 11 is a schematic view showing a 3D dodecahedron structure.

With the present invention the honeycomb structure can be 3D, such as a dodecahedron structure, similar to nano buckyballs geometry, and can be superelastic and/or have SME (shape memory effect via temperature change). It may also be made up of a repeating pattern of diamonds, hexagons, or any other shape. See FIGS. 11, 12 and 13.

Figure 15:
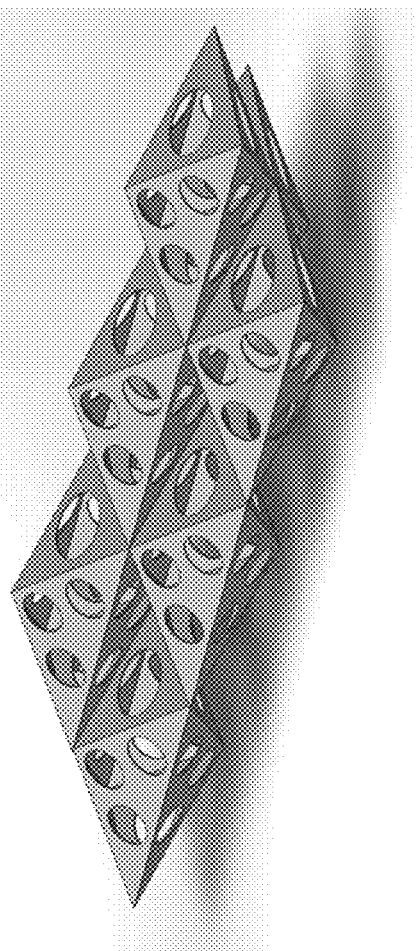
FIG. 15 is a schematic view showing a structure formed out of a plurality of diamond shaped functional units assembled together.
Figure 14:
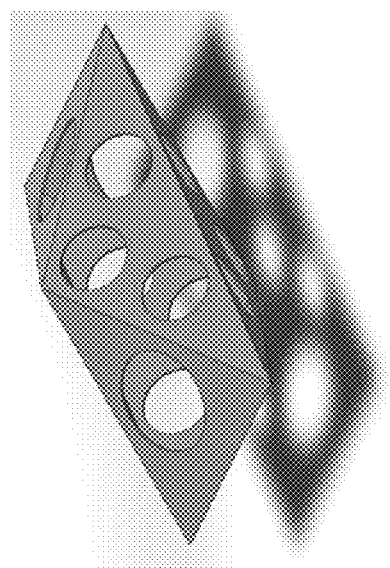
FIG. 14 is a schematic view showing a diamond shaped functional unit.

By staggering the orientation of the hexagonal element (instead of aligning them on top of each other), a more complicated pore structure can be created. Additionally, porosity can be increased with the addition of holes on the faces of the honeycomb elements. See FIGS. 14 and 15.

Figure 16:
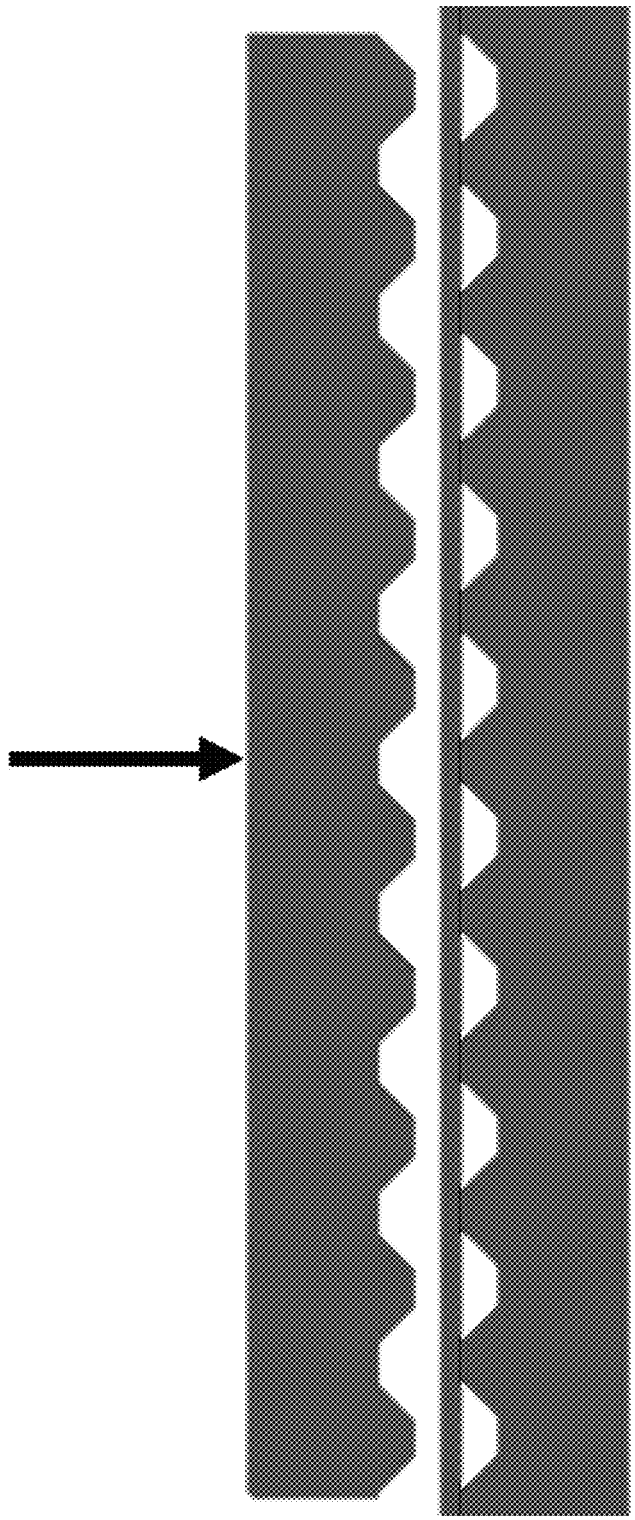
FIG. 16 is a schematic view showing how a honeycomb sheet can be manufactured from a flat sheet of material.

Methods of manufacturing honeycomb structures are known in the art. One popular method is to stamp the shape of the honeycomb footprint from a thin sheet of material, and then press it between two dies. Two of the resulting sheets can then be placed on top of each other, and welded or braised together so as to create the overall shape. Holes can be cut into the thin sheet either before or after corrugating the convolutions or after the sheets are welded/braised together. See FIG. 16.

Figure 17:
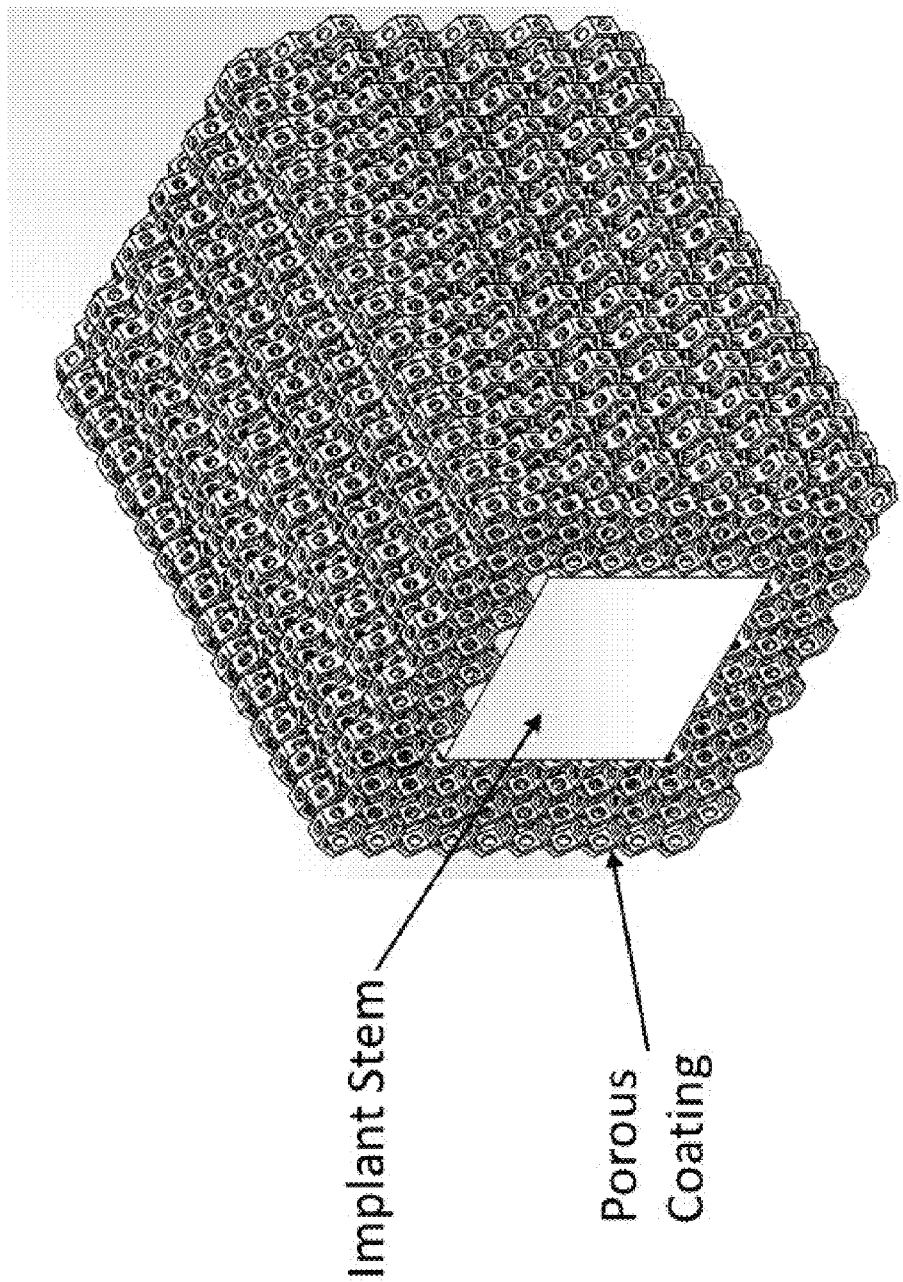
FIG. 17 is a schematic view showing how a 3D honeycomb structure can be formed by assembling a plurality of honeycomb sheets.

These sheets of honeycomb can be layered on top of each other, and attached to the outside surface of the implant stem. See FIG. 17.

Method of Shape Setting Shape Memory Alloy (SMA)

Nickel-titanium shape memory metal alloy, Nitinol (NiTi), is a functional material whose shape and stiffness can be controlled with temperature. The metal undergoes a complex crystalline-to-solid phase change called martensite-austenite transformation. As the metal in the high-temperature (austenite) phase is cooled, the crystalline structure enters the low-temperature (martensite) phase, where it can be easily bent and shaped. As the metal is reheated above its transition temperature, its original shape and stiffness are restored. SMA materials exhibit various characteristics depending on the composition of the alloy and its thermal-mechanical work history. The material can exhibit 1-way or 2-way shape memory effects. A 1-way shape memory effect results in a substantially irreversible change upon crossing the transition temperature, whereas a 2-way shape memory effect allows the material to repeatedly switch between alternate shapes in response to temperature cycling. SMA can recover large strains in two ways; shape memory effect (SME) and pseudoelasticity also known as superelasticity (SE). The NiTi family of alloys can withstand large stresses and can recover strains near 8% for low cycle use or up to about 2.5% strain for high cycle use. The titanium beta and near beta alloys can have SME and SE from achieving a martensite double prime ($\alpha''$) phase from quenching after heating just below the transus temperature and subsequently setting (aging and working) the material preparing for phase transformations and shape change.

Figure 18:
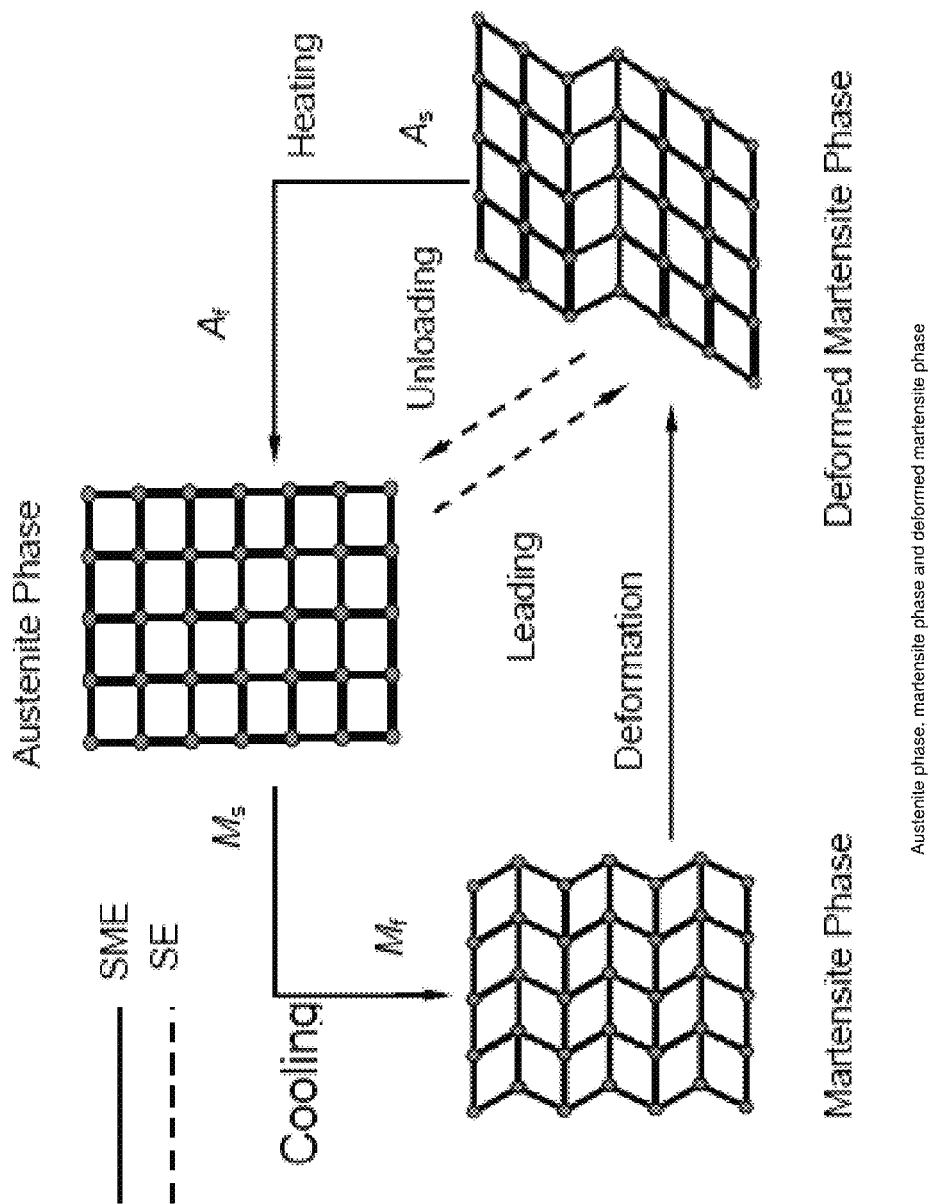
FIG. 18 is a schematic view showing phase transformations in a shape memory and superelastic material.

The shape memory alloys, termed as functional materials, show two unique capabilities: shape memory effect (SME) and superelasticity (SE), which are absent in traditional materials. Both SME and SE largely depend on the solid-solid, diffusionless phase transformation process known as martensitic transformation (MT) from a crystallographically more ordered parent phase (austenite) to a crystallographically less ordered product phase (martensite). The phase transformation (from austenite to martensite or vice versa) is typically marked by four transition temperatures, named as Martensite finish (Mf), Martensite start (Ms), Austenite finish (Af), and Austenite start (As). If the temperatures for Mf<Ms<As<Af, then a change in the temperature within Ms<T<As induces no phase change and both martensite and austenite may coexist within Mf<T<Af. The phase transformations may take place depending on changing temperature (SME) or changing stress (SE). See FIG. 18.

Shape Memory Effect (SME)

For T>Af, the SMA is in the parent austenite phase with a particular size and shape. Under stress free condition, if the SMA is cooled to any temperature T<Mf, martensitic transformation (MT) occurs as the material converts to product martensite phase. MT is basically a macroscopic deformation process, though actually no transformation strain is generated due to the so-called self accommodating twinned martensite. If a mechanical load is applied to this material and the stress reaches a certain critical value, the pairs of martensite twins begin 'detwinning' (conversion) to the stress-preferred twins. The 'detwinning' or conversion process is marked by the increasing value of strain with insignificant increase in stress. The multiple martensite variants begin to convert to a single variant, the preferred variant being determined by the alignment of the habit planes with the axis of loading. As the single variant of martensite is thermodynamically stable at T<As, upon unloading there is no reconversion to multiple variants and only a small elastic strain is recovered, leaving the materials with a large residual strain (apparently plastic). Next, if the deformed SMA is heated above Af, SMA transforms to parent phase (which has no variants), the residual strain is fully recovered and the original geometric-configuration is recovered. It happens as if the material recalls from 'memory' of its original shape before the deformation and fully recovers. Therefore, this phenomenon is sometimes referred to as shape memory effect (1-way SME). However, if some end constraints are used to prevent this free recovery to the original shape, the material generates large tensile recovery stress, which can be exploited as an actuating force for active or passive control purposes. SMM coatings can be processed via SME.

Superelasticity (SE)

The second feature of SMA is pseudoelasticity. The superelastic SMA has the unique capability to fully regain the original shape from a deformed state when the mechanical load that causes the deformation is withdrawn. For some superelastic SMA materials, the recoverable strains can be on the order of 10%. This phenomenon, which is sometimes referred to as the pseudoelasticity or superelasticity (SE) effect, is dependent on the stress-induced martensitic transformation (SIMT), which in turn depends on the states of temperature and stress of the SMA. To explain the SE, consider the case when the SMA that has been entirely in the parent phase (T>Af) is mechanically loaded. Thermodynamic considerations indicate that there is a critical stress at which the crystal phase transformation from austenite to martensite can be induced. Consequently, the martensite is formed because the applied stress substitutes for the thermodynamic driving force usually obtained by cooling for the case of SME. The load, therefore, imparts an overall deformation to the SMA specimen as soon as a critical stress is exceeded. During unloading, because of the instability of the martensite at this temperature in the absence of stress, again at a critical stress, the reverse phase transformation starts from the stress-induced martensite (SIM) to parent phase. When the phase transformation is complete, the SMA returns to its parent austenite phase. Therefore, superelastic SMA shows a typical hysteresis loop (known as pseudoelasticity or superelasticity) and if the strain during loading is fully recoverable, it becomes a closed one. It should be noted that SIMT (or the reverse SIMT) are marked by a reduction of the material stiffness. Usually the austenite phase has much higher Young's modulus in comparison with the martensite phase.

Nitinol cardiovascular stents, orthodontic wires and other commercially available wire and thin wall tubing products utilize the material's superelastic characteristics. The material's Af temperature is set in relation to body temperature. Stress induced martensite transformation (SIMT) is used to help collapse the products' diameter to facilitate minimally invasive insertion into the body. The material is expanded in the body once free from its constrained/stressed state, desirably applying a long-term compression of tissues or bones.

Figure 19:
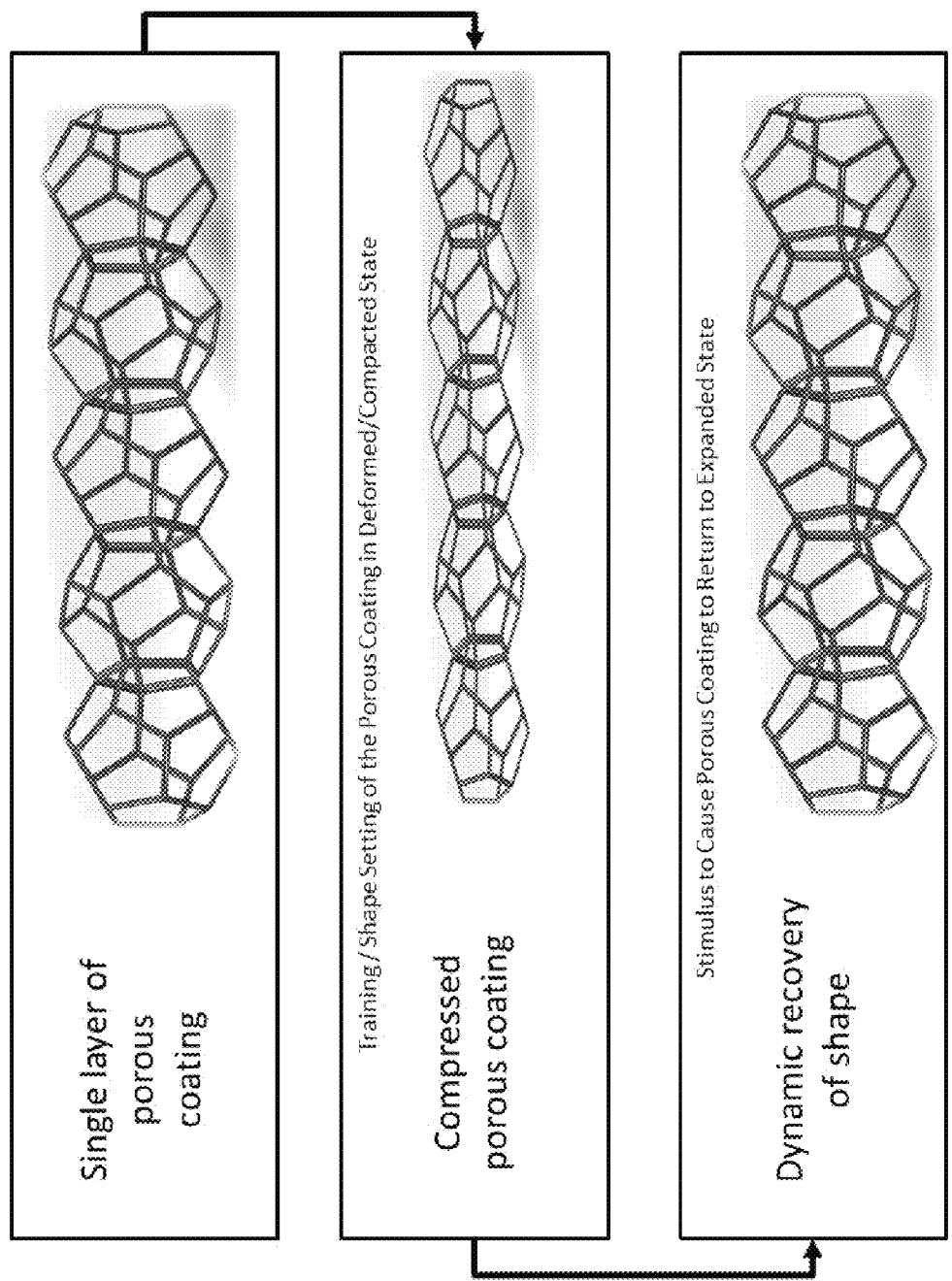
FIG. 19 is a schematic view showing how a porous coating formed out of a shape memory material can exhibit one-way or two-way shape memory effects and can exhibit shape change due to superelasticity or the shape memory effect.

The dynamic, SMM porous coatings can exhibit 1-way or 2-way shape memory effects; and it can also exhibit SE. See FIG. 19.

Figure 20:
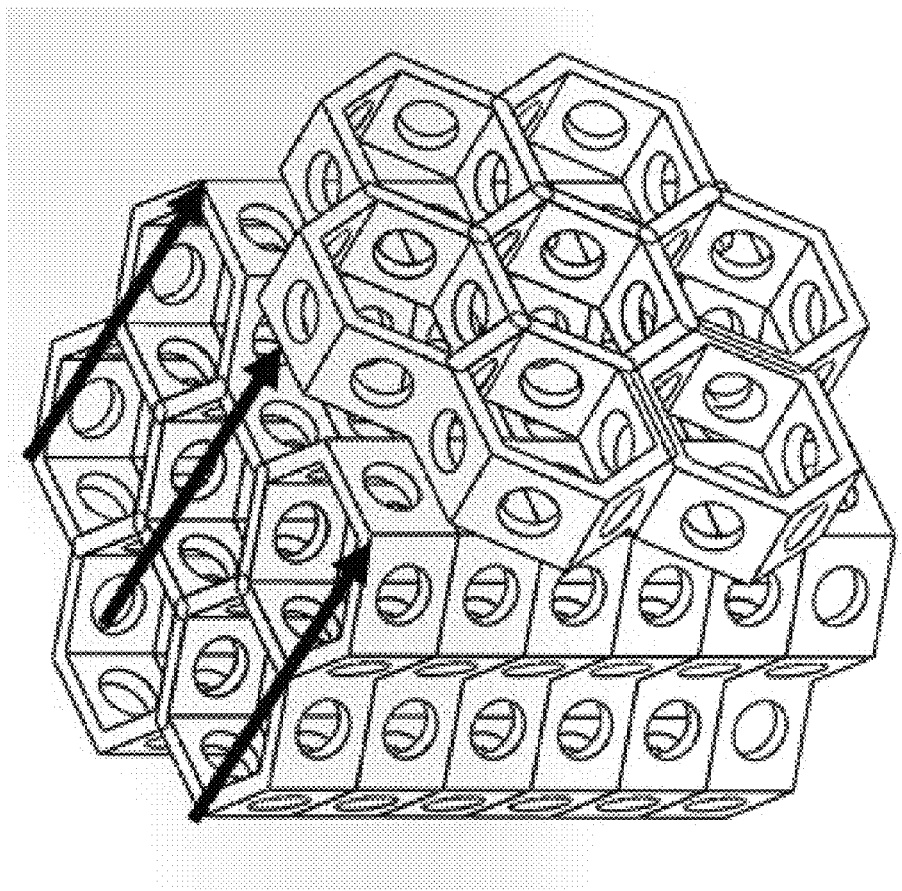
FIG. 20 is a schematic view showing how shape recovery of a porous coating can be used to apply a force to adjacent bone.

When this effect is applied to the honeycomb shaped structures, similar behavior is observed. Additionally, the shape recovery of the honeycomb, combined with multiple directions of the honeycomb structure, can be used to force a largely open surface into direct contact with bone to further induce osteointegration and establish early fixation. See FIG. 20.

Effect of Dynamic Coating on Osseointegration

Bone adapts and remodels in response to the stress applied to it. Wolff's Law states that bones develop a structure most suited to resist the forces acting upon them, adapting both the internal architecture and the external conformation to the change in external loading conditions. When a change in loading pattern occurs, stress and strain fields in the bone change accordingly. Bone tissue seems to be able to detect the change in strain on a local basis and then adapts accordingly. The bone's internal architecture is adapted in terms of change in density and in the disposition of trabecules and osteons, and the bone's external conformation is adapted in terms of shape and dimensions. When strain is intensified new bone is formed. On a microscopic scale bone density is raised and on a macroscopic scale the bone external dimensions are incremented. When strain is lowered bone resorption takes place. On a microscopic scale bone density is lowered and on a macroscopic scale the bone external dimensions are reduced, undesirable stress shielding often causing aseptic implant loosening. When the expanding SMM coating applies stress to the bone tissue, apposition will take place and bone density levels will maintain or even increase. Thus, the use of a dynamic porous coating enhances bone growth adjacent the implant which will assist for bone growth to migrate into the interconnecting porous coating.

A dynamic porous coating allows surgeons to coat or fill the pores of the coating with hydroxyapatite, tricalcium phosphate and other bone-promoting agents known in the art which will remain intact during implant impaction. Current cementless hip and knee implants, for example, are wedged into the femoral or tibial bone by means of a hammering of the implant with a mallet to drive the implant into the prepared bone cavity. A tight interference fit between the implant and femoral bone, however, may undesirably scrape and/or "squeegee" off drugs applied to the surfaces of the dynamic porous coatings. A dynamic porous coating will allow the implant (collapsed through SIMT), to be coated, inserted into the femoral canal without the "squeegeeing" effect, and then dynamically expand either thru SE or SME. The pores can be treated with biologically active agents to prevent periprosthetic infection.

Figure 21:
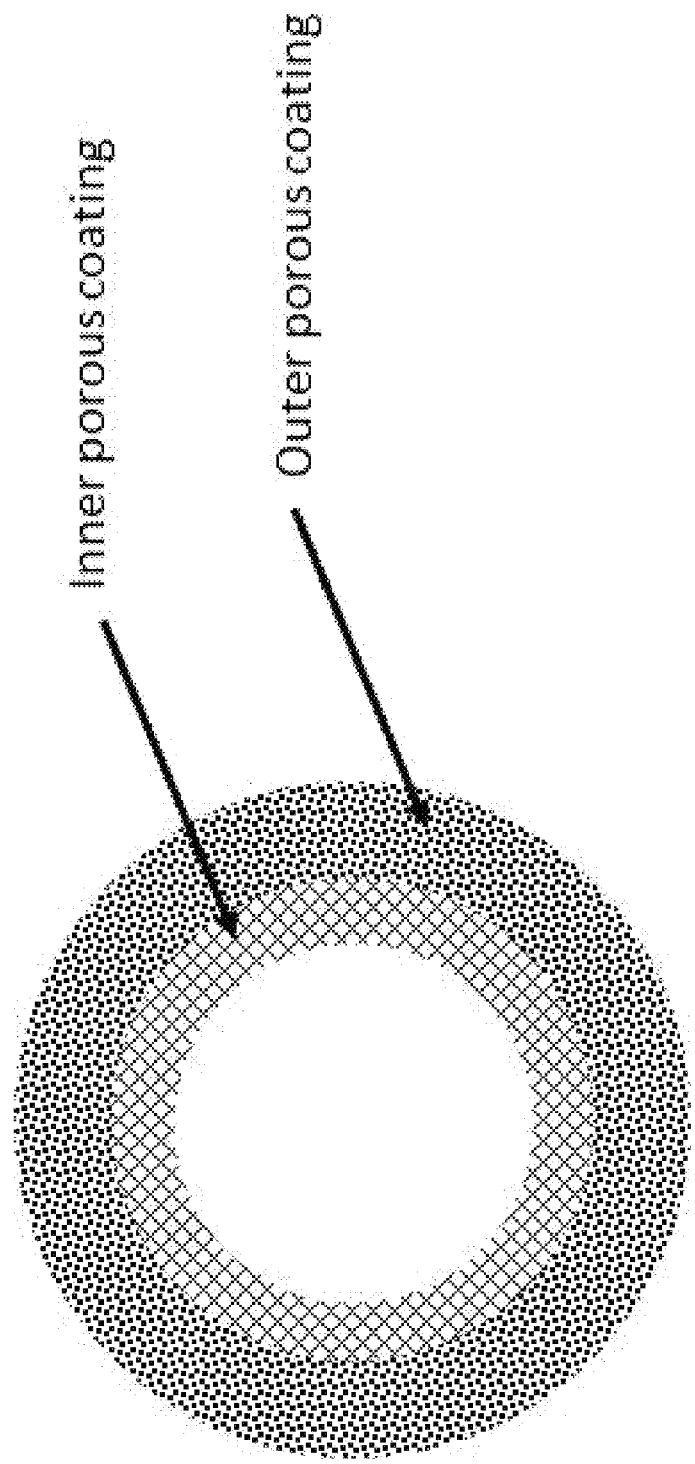
FIG. 21 is a schematic view showing how the porous coating for an implant can comprise two different porous coatings, e.g., an inner porous coating having one set of properties and an outer porous coating having another set of properties.

A dynamic porous implant can be created with two different surface characteristics on the inner and outer surfaces. Using a medullary stent as an example, the outer surface of the stent that comes into contact with the bone can be prepared with a dynamic coating suitable for osseointegration. The inner surface of the stent can be prepared with a coating tailored for the generation of new bone marrow. The pore size and frequency of the layers can be varied as required. See FIG. 21.

Thus it will be seen that the present invention comprises the provision and use of a novel porous coating made of shape memory material that is applied and bonded to the surface of an orthopedic implant and which is capable of expanding once inserted into the bone via superelasticity or shape memory effect (temperature change) so as to fill gaps between the porous coating and adjacent bone and to create an interference fit between the implant and bone tissue. The expansion may be initiated by either the compressed fit of the implant into a bone aperture such that the compressed porous coating expands against the adjacent bone or by the removal of a containment sleeve (superelasticity effect), or the effect of the material warming from a temperature below body temperature to body temperature (shape memory effect). The strain from the expanding implant can cause bone remodeling, enhance osseointegration and will facilitate immediate fixation and long term apposition. The structure of the coating can be 3D with interconnection pores similar to trabecular bone or a 3D honeycomb structure to facilitate bone ingrowth into the coating. The strength and stiffness of the coating can be accurately matched to bone.

It is also possible to create dynamic porous implants that are fully porous, have a non-dynamic core and a dynamic outer surface. In this form of the invention, there is no coating (i.e., additive layer) on an underlying device. Instead, the dynamic porous implant is a singular structure, where there may be a structural and/or material gradient that allows the core of the implant to be non-dynamic and the surface of the implant to be dynamic. It is possible to create a monolithic structure (i.e., a singular structure) that has regions that are static and regions that are elastic. As an example, it is possible to create a porous Nitinol core that is fabricated using a structure that is highly rigid and have a different surface structure that is highly elastic. Additive manufacturing (i.e., three dimensional printing) allows for creating gradient structures, as do the other porous metal methods disclosed herein.

Implants can also be made of the porous metal of the present invention and do not require that the porous metal be bonded to a solid substrate. Looking now at FIGS. 22-25, various dynamic porous metal implants are shown.

Figure 22:
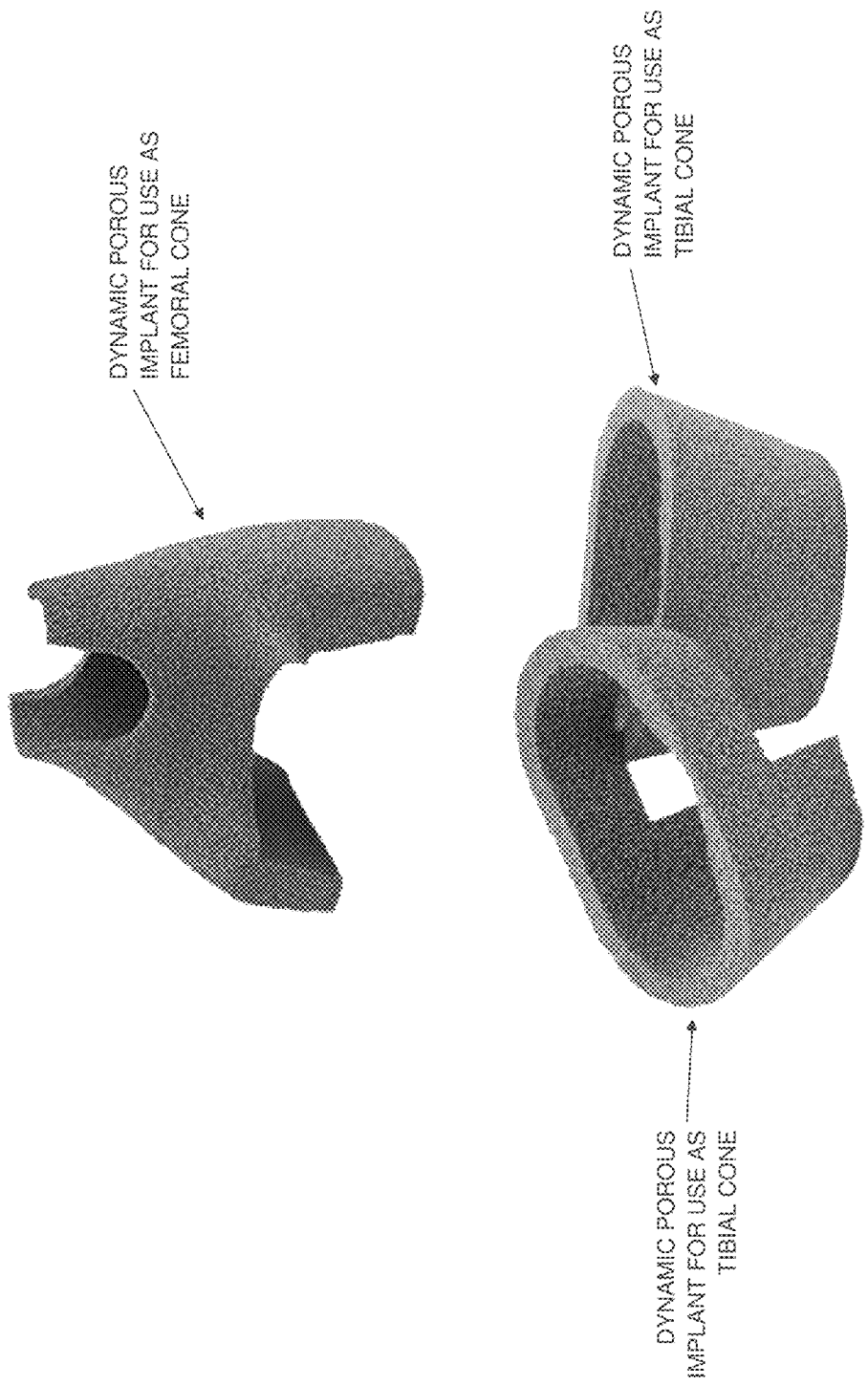
FIG. 22 is a schematic view showing dynamic porous implants for use as femoral and tibial cones.

FIG. 22 shows dynamic porous implants for use as femoral and tibial cones. These cones can be used to fill bone voids between the tibia/femur and the tibial/femoral implant. The dynamic porous implant conforms to the patient's anatomy. Where there is a tight fit between the femoral/tibial implant and the bone, the cone compresses. Where there are gaps between the femoral/tibial implant and the bone, the cone can expand to fill the gap. In either situation, any compression to the dynamic porous implant results in the implant applying a shape recovery stress to the neighboring bone, enhancing bone growth.

Figure 23:
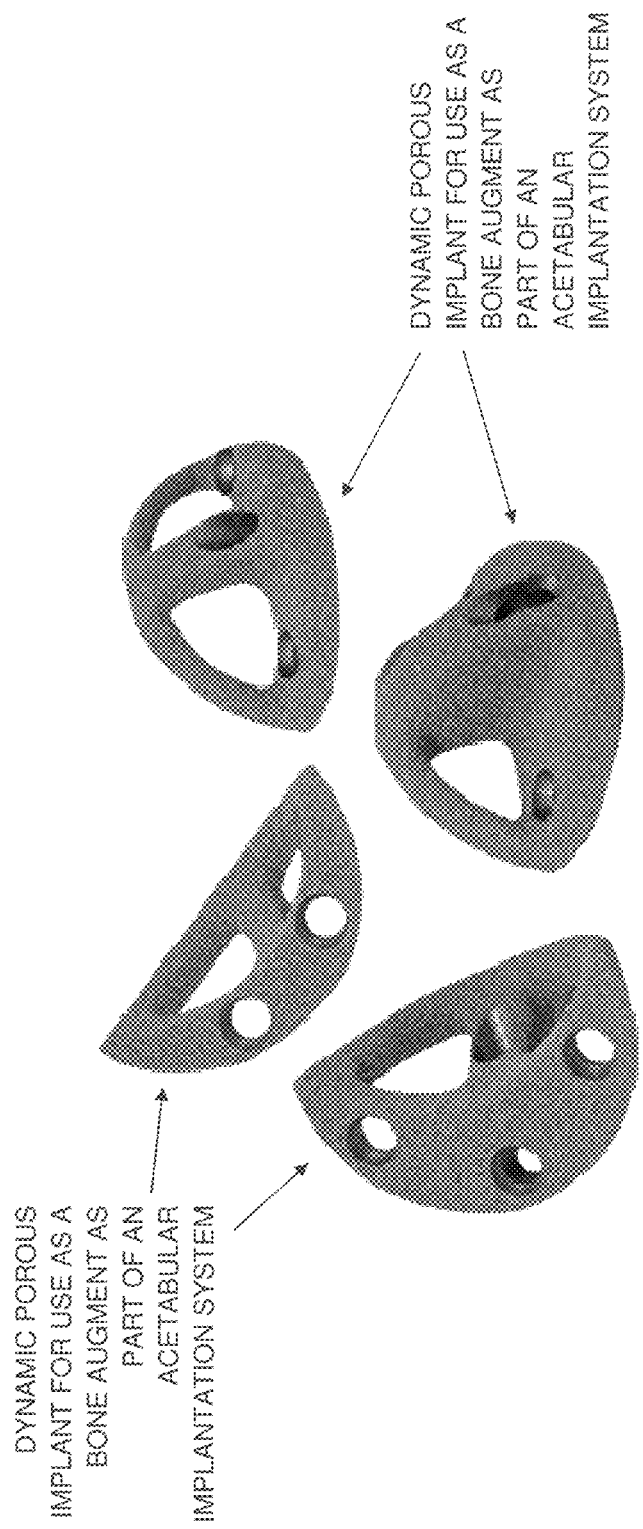
FIG. 23 is a schematic view showing a dynamic porous implant for use as a bone augment as part of an acetabular implantation system.

FIG. 23 shows dynamic porous implants for use as bone augments. These bone augments are sized to aid in the support of an acetabular cup implant. The dynamic porous implant can conform to the acetabular defect, compressing where there is a tight fit, and expanding to fill gaps between the acetabular cup and the bone.

Figure 24:
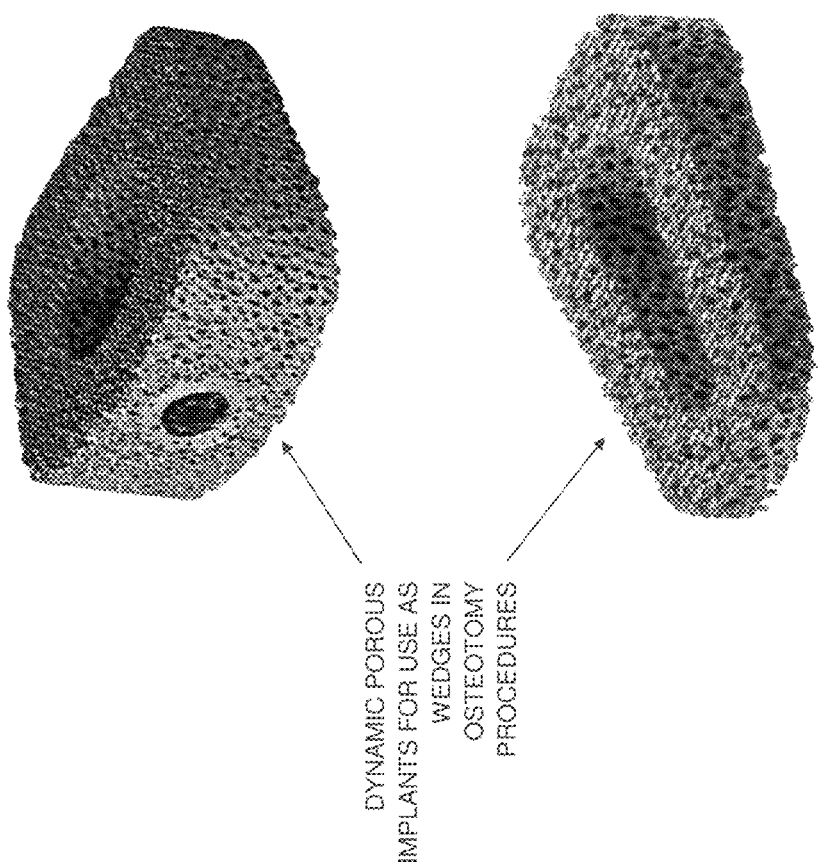
FIG. 24 is a schematic view showing dynamic porous implants for use as wedges in osteotomy procedures.

FIG. 24 shows dynamic porous implants for use as bone augments. These bone augments are used to maintain bone alignment following an opening wedge osteotomy. The osteotomy is performed and the dynamic porous implant is inserted into the bone to correct the alignment of the bone. The cut used to create the osteotomy might not be perfectly straight and a traditional "static" augment would leave gaps between the implant and the bone. The dynamic porous implant can conform to the osteotomy site, filling any gaps between the implant and bone.

Figure 25:
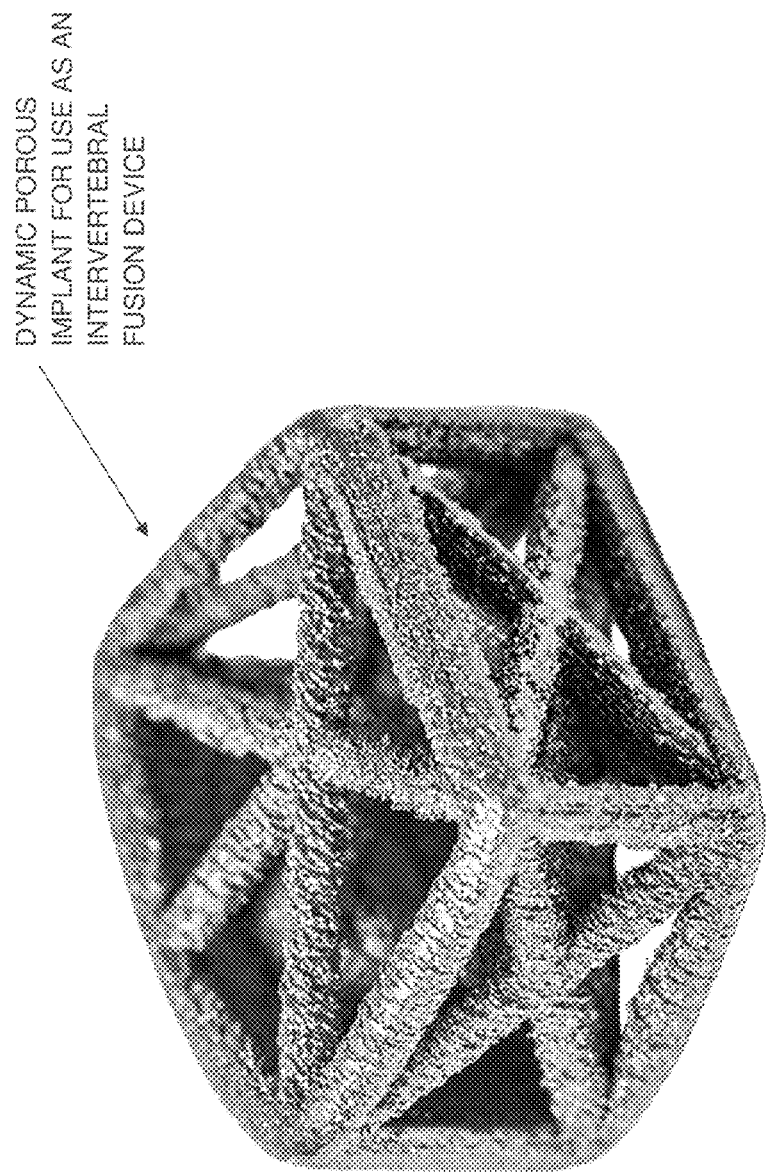
FIG. 25 is a schematic view showing a dynamic porous implant for use as an intervertebral fusion device.

FIG. 25 shows a dynamic porous implant for use as an intervertebral fusion device. This implant can be used to fuse adjacent vertebra after removal of the intervertebral disc. The implant can expand to fill gaps between the adjacent vertebra and provide the needed rigidity to support the weight of the adjacent bodies.

MODIFICATIONS

While the present invention has been described in terms of certain exemplary embodiments, it will be readily understood and appreciated by those skilled in the art that it is not so limited, and that many additions, deletions and modifications may be made to the embodiments discussed herein without departing from the scope of the invention.

What is claimed is:

1. A method for providing therapy to a patient, the method comprising:
   inserting a medical implant into a patient, wherein the medical implant comprises a dynamic porous material that comprises a porous structure formed of a shape memory alloy, wherein the porous structure comprises a honeycomb cellular structure that includes elements having a staggered orientation relative to other elements, wherein the dynamic porous material conforms to an adjacent bone to create an interference fit between the medical implant and the adjacent bone.

2. The method according to claim 1 wherein the porous structure comprises a regular repeating pattern.

3. The method according to claim 1 wherein the therapy provided by the outward force applied by the dynamic porous coating is bone remodeling.

4. The method according to claim 1 wherein the implant has a modulus between 1 and 20 GPa.

5. The method according to claim 1 wherein the porous structure comprises a dodecahedron cellular structure.

6. The method according to claim 1 wherein the implant comprises a singular structure.

7. The method according to claim 6 wherein the implant has a non-dynamic core and a dynamic surface.

8. The method according to claim 7 wherein the singular structure has a structural or material gradient.

9. The method according to claim 1 wherein the dynamic porous material is coated with a bone-promoting agent.

10. The method according to claim 1 wherein the dynamic porous material includes a first surface and a second surface that is different from the first surface.

11. The method according to claim 1 wherein the dynamic porous material has a gradient structure including stating regions and elastic regions.

12. The method according to claim 1 wherein the elements are hexagonal elements.

13. The medical implant comprising:
a dynamic porous material comprising a porous structure formed of a shape memory material, the medical implant being configured for insertion into a patient, wherein the porous structure comprises a honeycomb cellular structure that includes elements having a staggered orientation relative to other elements.

14. The implant according to claim 13 wherein the porous structure comprises a regular repeating pattern.

15. The implant according to claim 13 wherein the therapy provided by the outward force applied by the dynamic porous coating is bone remodeling.

16. The implant according to claim 13 where in the implant is a bone void filler.

17. The implant according to claim 13 wherein the implant is a bone augmentation device.

18. The implant according to claim 13 wherein the implant has a modulus between 1-20 GPa.

19. The implant according to claim 13 wherein the porous structure comprises a dodecahedron cellular structure.

20. The implant according to claim 13 wherein the implant comprises a singular structure.

21. The implant according to claim 20 wherein the implant has a non-dynamic core and a dynamic surface.

22. The implant according to claim 21 wherein the singular structure has a structural or material gradient.

23. The implant according to claim 13 wherein the dynamic porous material is coated with a bone-promoting agent.

24. The implant according to claim 13 wherein the dynamic porous material includes a first surface and a second surface that is different from the first surface.

25. The implant according to claim 13 wherein the dynamic porous material has a gradient structure including stating regions and elastic regions.

26. The implant according to claim 13 wherein the elements are hexagonal elements.

* * * * *

UNITED STATES PATENT AND TRADEMARK OFFICE
CERTIFICATE OF CORRECTION

PATENT NO. : 9,907,657 B2
APPLICATION NO. : 15/063885
DATED : March 6, 2018
INVENTOR(S) : Robert Mason Darling, Andrew Matthew Fonte and Matthew Palmer Page 1 of 1

It is certified that error appears in the above-identified patent and that said Letters Patent is hereby corrected as shown below:

In the Claims

In Claim 16, Column 12, Line 8; replace "where in" with --wherein--

Signed and Sealed this
Fifteenth Day of October, 2019

Andrei Iancu
*Director of the United States Patent and Trademark Office*